United States Patent [19]

Holtsch

[11] Patent Number: 5,121,954
[45] Date of Patent: Jun. 16, 1992

[54] CLOSURE FOR ENDS OF BAND OR THE LIKE

[75] Inventor: Peter Holtsch, Wingsbach, Fed. Rep. of Germany

[73] Assignee: Holtsch Metallwarenherstellung, Wingsbach, Fed. Rep. of Germany

[21] Appl. No.: 715,783

[22] Filed: Jun. 14, 1991

[30] Foreign Application Priority Data

Jun. 23, 1990 [DE] Fed. Rep. of Germany ... 9009941[U]

[51] Int. Cl.$^5$ ..................... B65D 33/34; A61B 17/12
[52] U.S. Cl. ..................................... 292/318; 606/203
[58] Field of Search ............... 606/203; 292/318, 323; 24/181, 205 R, 265 EC; 128/327

[56] References Cited

U.S. PATENT DOCUMENTS 4,125,115 11/1978 Mayo et al. .................... 606/203
4,640,281 2/1987 Sturm et al. .................... 606/203

FOREIGN PATENT DOCUMENTS 86104375.0 6/1978 European Pat. Off. .
2824037 3/1986 Fed. Rep. of Germany .
8708299.3 6/1987 Fed. Rep. of Germany .

Primary Examiner—Richard E. Moore
Attorney, Agent, or Firm—Michael J. Striker

[57] ABSTRACT

A closure for a band and the like comprises a closure housing adapted for passing a band therethrough, a housing cap adapted to be connected to an end of the band, and elements for releasably connecting the closure housing with the housing cap. The connecting elements include a pin projecting from the closure housing and having a front end with two oppositely inclined surfaces and two transverse grooves, and two sliders accomodated in the housing cap slidingly over one another and each having a projection and a shaped formation facing toward one another and formed so that in a locked condition the projections of the sliders of the housing cap engage in the grooves of the pin of the closure housing while the shaped formations of the sliders of the housing cap abut against the inclined surfaces of the pin of the closure housing.

13 Claims, 3 Drawing Sheets

CLOSURE FOR ENDS OF BAND OR THE LIKE

BACKGROUND OF THE INVENTION

The present invention relates to a closure for opposite end of a band or the like. More particularly, it relates to such a closure which has a closure housing with a projecting engaging element for a housing cap in which the end of a band is mounted, and a push button device for releasing the housing cap from the closure housing.

Closures of the above mentioned general type are known in the art. One of such closures is disclosed in the German document No. DE-GM 8,708,299.3 as applied to a turniquet for limbs. The above mentioned document describes a closure in which the arresting element has a central, springy ledge and two inclined outwardly oriented, springy or spring-elastic hooks with outwardly oriented projections. The ledge engages in a central guide of the cap provided on the band end during connecting and engaging of the housing cap with a closure housing. Two convex sliding surfaces facing the interior of the cap are arranged on the cap symmetrically relative to its central axis for guiding purposes. The distance between the sliding surfaces is smaller than the distance of the outer surfaces of the hooks. The sliding surfaces extend to the height of two lateral push buttons and each form there a step, behind which the projection engages in the locked condition of the cap. The push buttons have inclined surfaces on their inner ends. During opposite pressing of the push buttons the inclined surfaces extend flush with the convex sliding surfaces, so that in each case two cooperating sliding surfaces are produced for the springy hook.

The above described closure operates in a satisfactory manner. However, it has the disadvantage that the central projecting ledge and two spring-elastic lateral hooks can be broken as a result of careless manipulations, and the lock becomes unuseable.

SUMMARY OF THE INVENTION

Accordingly, it is an object of the present invention to provide a closure of the above mentioned general type, which not only provides a fast and reliable connection of the closure housing with the housing cap, but also has a special construction of their connecting means characterized by high safety against breaking of its parts.

In keeping with these objects and with others which will become apparent hereinafter, one feature of the present invention resides, briefly stated, in a closure which has a pin extending from the outside of the closure housing and having a front end provided with two oppositely inclined surfaces and also two transverse grooves, while the housing cap has two superposed and oppositely movable sliders each having a projection and a shaped formation formed so that in a locked condition of the closure housing and the housing cap the projections of the sliders engage in the grooves of the pin while the shaped formation of the slider abut against the inclined surfaces of the pin.

When the closure is designed in accordance with the present invention, the single pin extending from the closure housing provides for a firm and reliable cooperation and extraordinarily strong connection with the housing cap. Moreover, when in accordance with another feature of the present invention the pin has a rectangular cross-section, its practically impossible to break the pin. Due to the special construction of the oppositely movable sliders arranged in the housing cap, a reliable arresting of the pin without additional springs is achieved. Also, by the abutment of the shaped formations on the opposite inclined surfaces, the arresting of the pin is maintained. By pressing on the push buttons, the pin after the disengagement of the projections from the grooves is pushed outwardly. Therefore a very efficient opening of the closure is achieved.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF A PREFERRED EMBODIMENT

Figure 1:
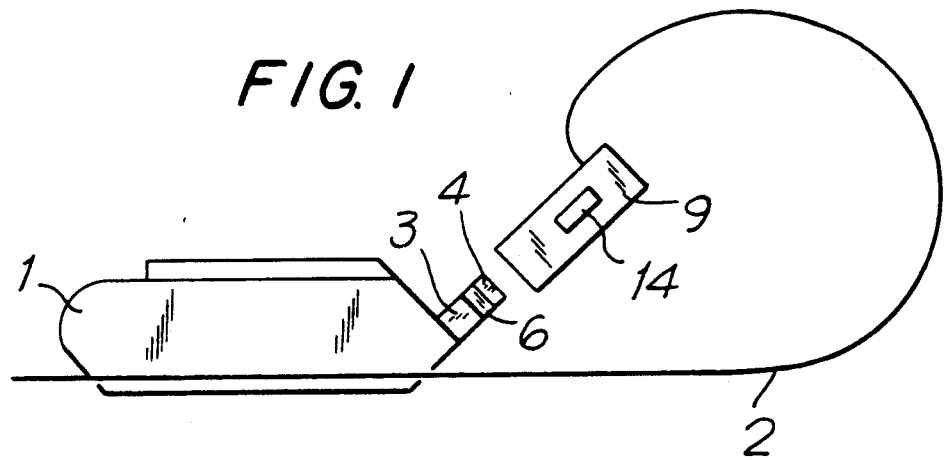
FIG. 1 is a side view of a closure in accordance with the present invention.
Figure 2:
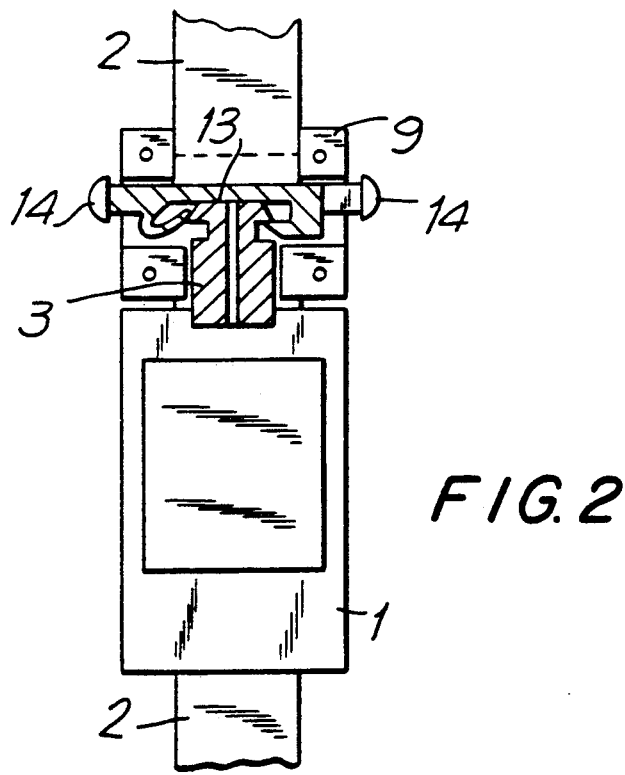
FIG. 2 is a plan view of the closure shown in FIG. 1, with a removed cover of a housing cap.
Figure 3A:
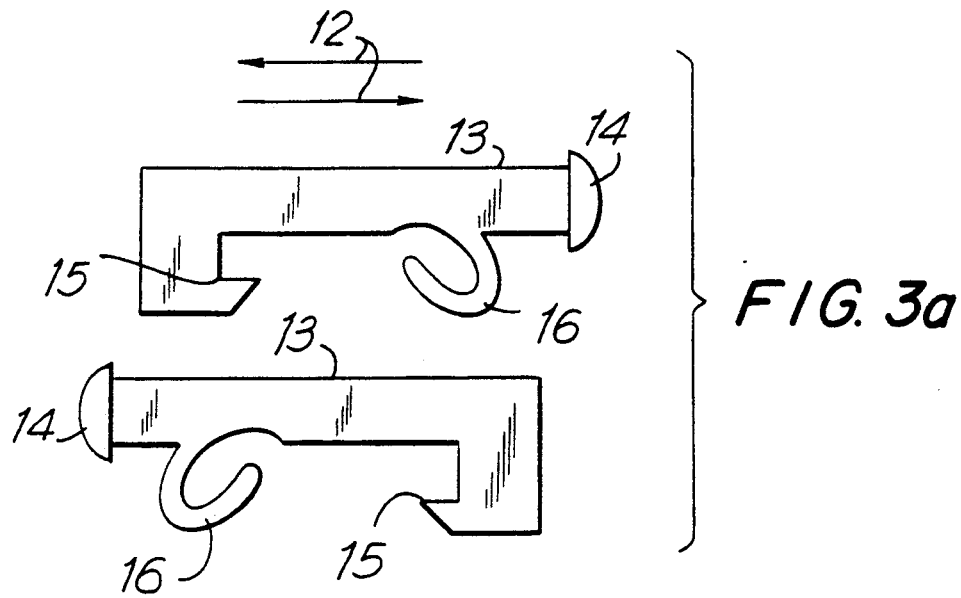
FIG. 3A is a view showing two sliders of connecting means for connecting a closure housing with a housing cap.
Figure 3B:
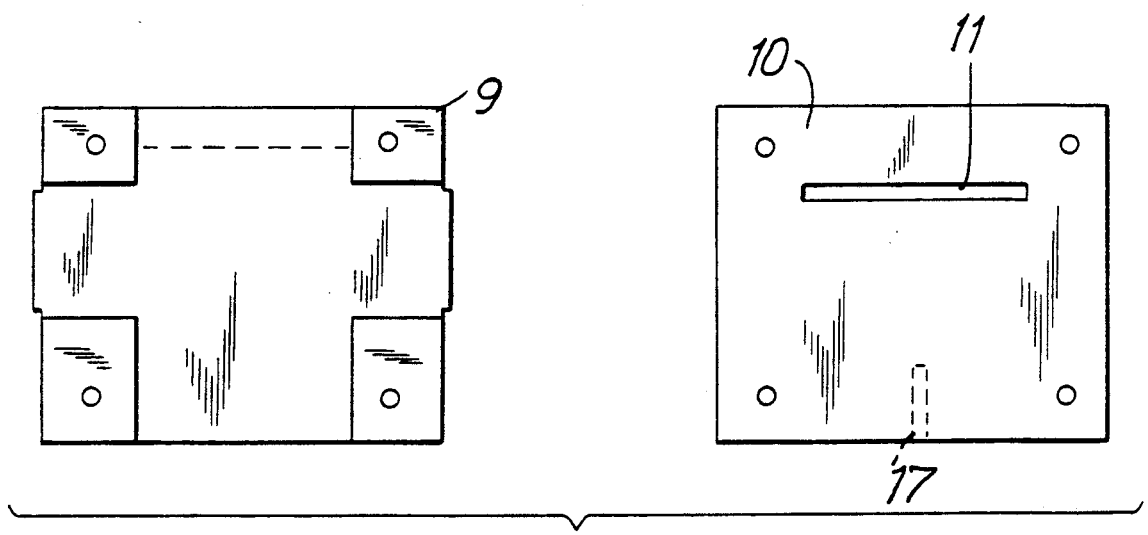
FIG. 3B is a view showing a shaped part and a cover of a housing cap.
Figure 3C:
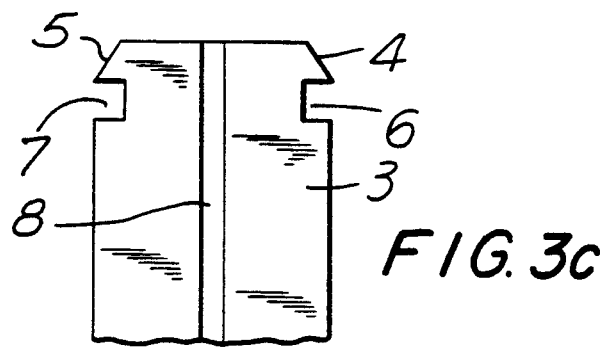
FIG. 3C is a view showing a pin projecting from the closure housing.

A closure for a band which is used as an example, for a turniquet for limbs in accordance with a present invention has a closure housing which is identified with reference numeral 1 and provided with a slot in its lower part. A band 2 is passed through the slot and forms a loop. A not shown mechanism is accommodated in the interior of the housing 1 and is actuatable by a button so that when the band is wound around a limb to be compressed the band 2 is fixed.

A pin 3 extends from the closure housing 1 and is fixedly connected with it. The pin 3 is inclined relative to the housing and has a rectangular cross-section. The pin 3 has a front end which is provided with two oppositely inclined surfaces 4 and 5 which together with an end surface of the pin form a roof-shaped profile. Two transverse grooves 6 and 7 are located between the front end of the pin 3 provided with the inclined surfaces 4 and 5, and the remaining portion of the pin 3. The pin 3 further has a longitudinal groove 8 which extends in a longitudinal direction.

The closure further has a housing cap composed substantially of two parts. The first part of the housing cap is a rectangularly shaped part 9 of synthetic plastic material, while the second part is a cover 10 which is screwed or riveted on the shaped part 9. The cover 10 has a slot 11 for the passage of the band 2. Two sliders 13 are arranged in the shaped part 9 of the housing cap.

The sliders 13 are located over one another and movable relative to one another in direction of the double arrow 12. The sliders 13 are identical and engage with the pin 3.

Each sliders 13 has a first end provided with a push button 14 and a second end provides with a projection 15. The projection 15 is transversely offset relative to the main portion of the slider 13 and extend in direction toward the push button 14. In the arrested condition of the closure housing 1 with the housing cap or more particularly of the pin 3 with the sliders, the projections 15 of the sliders 13 engage in the respective grooves 6 and 7.

An ear-like bent hook 16 is arranged between the push button 14 and the projection 15 of each slider 13. In the arrested position, the hook 16 abuts against the respective, oppositely located upper inclined surface 4 or 5 of the pin 3. A guiding lug 17 is arranged on the inner side of the cover 10. The guiding lug 17 engages in the longitudinal groove 8 of the pin 3.

In the arrested condition shown in FIG. 1 the projections 15 of the sliders of the housing cap engage in the grooves 6 and 7 of the pin 3 of the closure housing 1. On the other side, the hooks 16 of the sliders 13 of the housing cap abut against the inclined surfaces 4 and 5 of the pin 3 of the closure housing 1.

For releasing the housing cap from the pin 3 and therefore from the closure housing, an opposite pressure is applied to both push buttons 14. As a result, the projections 15 disengage from the grooves 6 and 7 under the elastic action of the synthetic plastic material and increased pressure applied by the ear-shaped bent hooks 16 to the inclined surfaces 4 and 5. As a result, the pin 3 springs out of he housing cap.

Figure 4A:
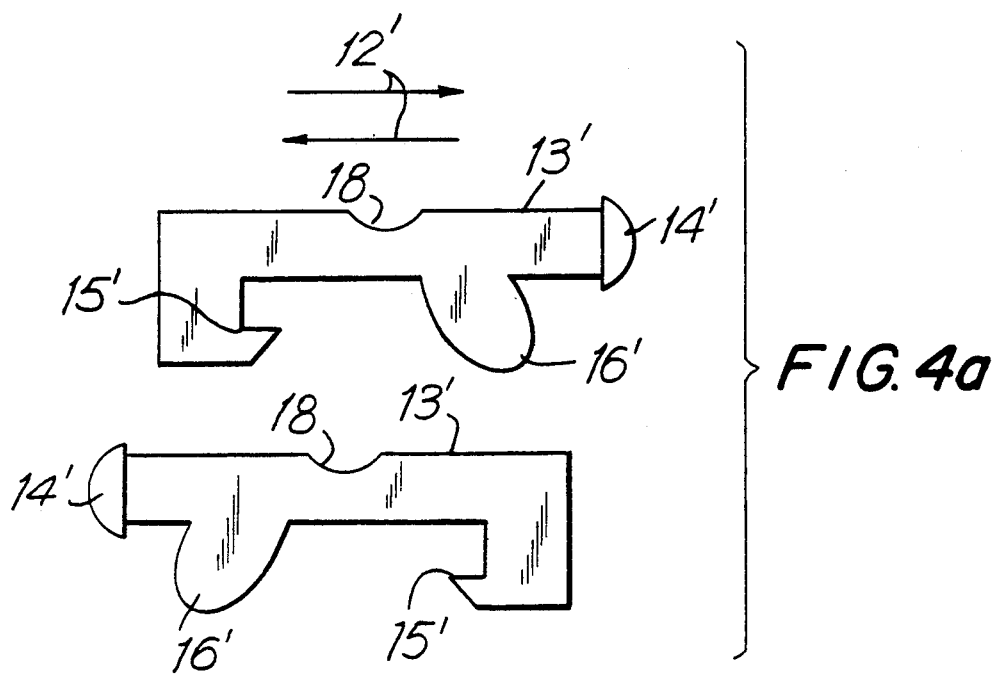
FIG. 4A is a view substantially corresponding to the view of FIG. 3A, but showing two sliders in accordance with a further modification of the present invention.
Figure 4B:
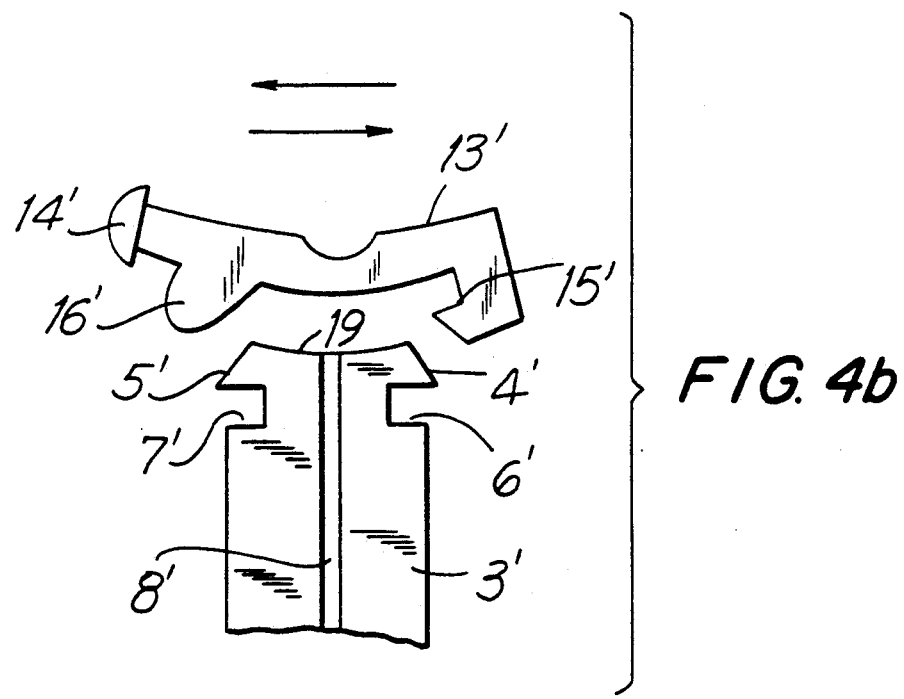
FIG. 4B is a view showing a pin projecting from the closure housing and cooperating with the sliders of FIG. 4A in accordance with the other embodiment of the invention.

FIGS. 4A and 4B show the closure in accordance with a further embodiment of he present invention. The parts of this modification which are similar to the parts of the first embodiment are identified with the same reference numerals with added primes.

In the second embodiment of the invention there are also two sliders identified with reference numeral 13'. Each of the sliders has a push button 14', a projection 15', and a shaped formation 16' instead of the hook 16 of the first embodiment. Each of the sliders 13' is made elastic by a depression 18 provided on its upper surface, as can be seen from FIG 4A. The pin 3' also has the inclined surfaces 4' and 5' and the grooves 6' and 7', as well as the longitudinal grooves 8'. In contrast to the first embodiment, the pin 3' has an upper surface 19 having a concave shape.

During assembly of the closure, the sliders 13' are arranged so that their lower surfaces are in contact with the upper concave surface 19 of the pin 3' and therefore the sliders 13' are bent and stressed. The projections 15' of the sliders of the housing cap engage in the grooves 6' and 7' of the pin 3' of the closure housing. On the other side, the formations 6' of the sliders 13' of the housing cap abut against the inclined surfaces 4' and 5' of the pin 3' of the closure housing. The arresting is performed in the bent condition of the sliders.

For releasing the housing cap from the pin 3' and therefore from the closure housing, an opposite pressure is applied to both push buttons 14'. As a result, the formations 16' slide along the inclined surfaces 4' and 5', the sliders 13' tend to assume their original straight shape, and the projections 15' disengage from the grooves 6' and 7' under the elastic action. As a result the pin 3' springs out of the housing cap.

It is to be understood that in the event of very inelastic synthetic plastic material, helical springs can be additionally arranged in the upper part of the housing cap, so as to apply a pressure to the pin 3 and push it out of the housing cap.

It will be understood that each of the elements described above, or two or more together, may also find a useful application in other types of constructions differing from the types described above.

While the invention has been illustrated and described as embodied in a closure for a turniquert for limbs, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A closure for a band and the like, comprising a closure housing adapted for passing a band therethrough; a housing cap adapted to be connected to an end of the band; and means for releasably connecting said closure housing with said housing cap, said connecting means including a pin projecting from the closure housing and having a front end with two oppositely inclined surfaces and two transverse grooves, said connecting means also including two sliders accommodated in said housing cap slidingly over one another and each having a projection and a shaped formation facing toward one another and formed so that in a locked condition said projections of said sliders of said housing cap engage in said grooves of said pin of said closure housing while said shaped formation of said sliders of said housing cap abut against said inclined surfaces of said pin of said closure housing.

2. A closure as defined in claim 1, wherein said pin of said closure housing has a rectangular cross-section.

3. A closure as defined in claim 1, wherein said pin has an end provided with said inclined surfaces so that said inclined surfaces together form a roof-shaped contour.

4. A closure as defined in claim 1, wherein said sliders are composed of a synthetic plastic material.

5. A closure as defined in claim 1, wherein said shaped formations of said sliders of said housing cap are elastically deformable hooks.

6. A closure as defined in claim 1, wherein said shaped formations of said slides of said housing cap are formed as solid elements.

7. A closure as defined in claim 1, wherein each of said sliders of said connecting means has one end provided with said projection and another end provided with a push button, said projection extends toward said push button of each of said sliders.

8. A closure as defined in claim 7, wherein said shaped formation of each of said sliders is located between said projection and said push button of said slider.

9. A closure as defined in claim 1, wherein each of said sliders has means imparting elasticity to said sliders, said pin having an end surface which is concave so that in an assembled condition said sliders abut against said concave end surface and are bent with a prestress.

10. A closure as defined in claim 9, wherein said imparting means includes at least one depression provided in each of said sliders.

11. A closure as defined in claim 10, wherein said depression of each of said sliders is located between said projection and said shaped formation of said slider.

12. A closure as defined in claim 1; and further comprising means for guiding said closure cap relative to said housing housing during movement between a locked position and an unlocked position.

13. A closure as defined in claim 12, wherein said guiding means includes a longitudinal groove provided in said pin and extending in a longitudinal direction of said pin, and a guiding rib provided on said housing cap and slidingly engaging in said longitudinal groove of said pin.

* * * * *